(12) United States Patent
Hsieh

(10) Patent No.: US 6,263,040 B1
(45) Date of Patent: Jul. 17, 2001

(54) METHODS AND APPARATUS FOR CONE-TILTED PARALLEL SAMPLING AND RECONSTRUCTION

(75) Inventor: Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/371,352

(22) Filed: Aug. 10, 1999

(51) Int. Cl.[7] .................................................... A61B 6/03
(52) U.S. Cl. .............................. 378/15; 378/62; 378/901; 378/4
(58) Field of Search ................................. 378/4, 15, 62, 378/901

(56) References Cited

PUBLICATIONS

Feldkamp et al., "Practical cone–beam algorithm", J. Opt. Soc. Am. A., vol. 1, No.6, pp. 612–619 (Jun. 1984).

Cobb et al., "Real–time Image Formation Effort Using Quadtree Backprojection and Reconfigurable Processing", Feb. 1999, "Proceedings—Third Annual Federated Laboratory Symposium on Advanced Sensors" pp 133–137.*

Oh et al., "Multi–resolution Mixed–radix Quadtree SAR Image Focusing Algorithms", Feb. 1999, "Proceedings—Third Annual Federated Laboratory Symposium on Advanced Sensors" pp 139–143.*

* cited by examiner

Primary Examiner—David V. Bruce
(74) Attorney, Agent, or Firm—Armstrong Teasdale LLP; Christian G. Cabou

(57) ABSTRACT

In one aspect, the present invention is a method for generating an image using a digital flat panel detector wherein a pre-defined delay triggering sequence is utilized to acquire a set of parallel and tilted parallel samples. The image is then generated using a tilted parallel beam reconstruction algorithm.

12 Claims, 3 Drawing Sheets

METHODS AND APPARATUS FOR CONE-TILTED PARALLEL SAMPLING AND RECONSTRUCTION

BACKGROUND OF THE INVENTION

This invention relates generally to computed tomography imaging, and more particularly, to generating volumetric images using data collected from a digital x-ray panel.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Digital x-ray panels capable of sampling a 40 cm by 40 cm area in a single projection are known. With such panels, detector signals are sampled one row at a time by activating a trigger signal. The activation signals for row 1 to N are activated sequentially while all the cell signals for each row are read simultaneously. A typical cell size is 200 μm×200 μm. For a panel that covers a 40 cm×40 cm region, the resulting image size is roughly 2000×2000 pixels.

When the panel is positioned opposite an x-ray source and both the source and the panel rotate about the patient to collect projection data from different angles, volumetric CT data is obtained. Since all the x-rays diverge from the x-ray source to the detector in three dimensions, a set of cone shaped samples is obtained for each projection. This type of scanner is referred to as cone beam CT.

Cone beam reconstruction algorithms are typically required due to the divergence of the sampling rays in both x-y and z directions. A known cone beam reconstruction algorithm is described in Feldkamp et al., "Practical cone-beam algorithm," J. Opt. Soc. Am. A., vol. 1, no. 6, pp. 612–619. This algorithm pre-weights the projections according to a pre-defined weighting function. The weighted projection is then filtered and backprojected to generate the reconstructed images. Because the backprojection process is in a cone-beam geometry, a magnification dependent (therefore, location dependent) scaling factor is needed. The requirement of the scaling factor significantly increases the computational complexity of the algorithm, which makes the reconstruction process very slow.

BRIEF SUMMARY OF THE INVENTION

In one aspect, the present invention is a method for generating an image using a digital flat panel detector wherein a pre-defined delay triggering sequence is utilized to acquire a set of parallel and tilted parallel samples. The image is then generated using a tilted parallel beam reconstruction algorithm. More specifically, an object, f(x,y,z), is:

$$f(x, y, z) = \frac{1}{2}\int_0^{2\pi} \left[d/(d^2+Z^2)^{1/2}\right] \left[\int_{-\infty}^{\infty} S_\beta(\omega, Z)e^{j2\pi\omega x}|\omega| d\omega\right] d\beta$$

where:

$$S_\beta(\omega, Z) = \int_{-\infty}^{\infty} P_\beta(t, Z)e^{-j2\pi\omega x} dt, \text{ and}$$

$P_\beta$ (t,Z) is the projection intersecting point (x,y,z).

The above described method does not require a magnification dependent scaling factor, and the algorithm is much more simple than the known algorithms which require the use of a scaling factor. In addition, and using the above described method, the reconstruction process much faster than the known algorithms that require the use of a scaling factor.

DETAILED DESCRIPTION OF THE INVENTION

Figure 1:
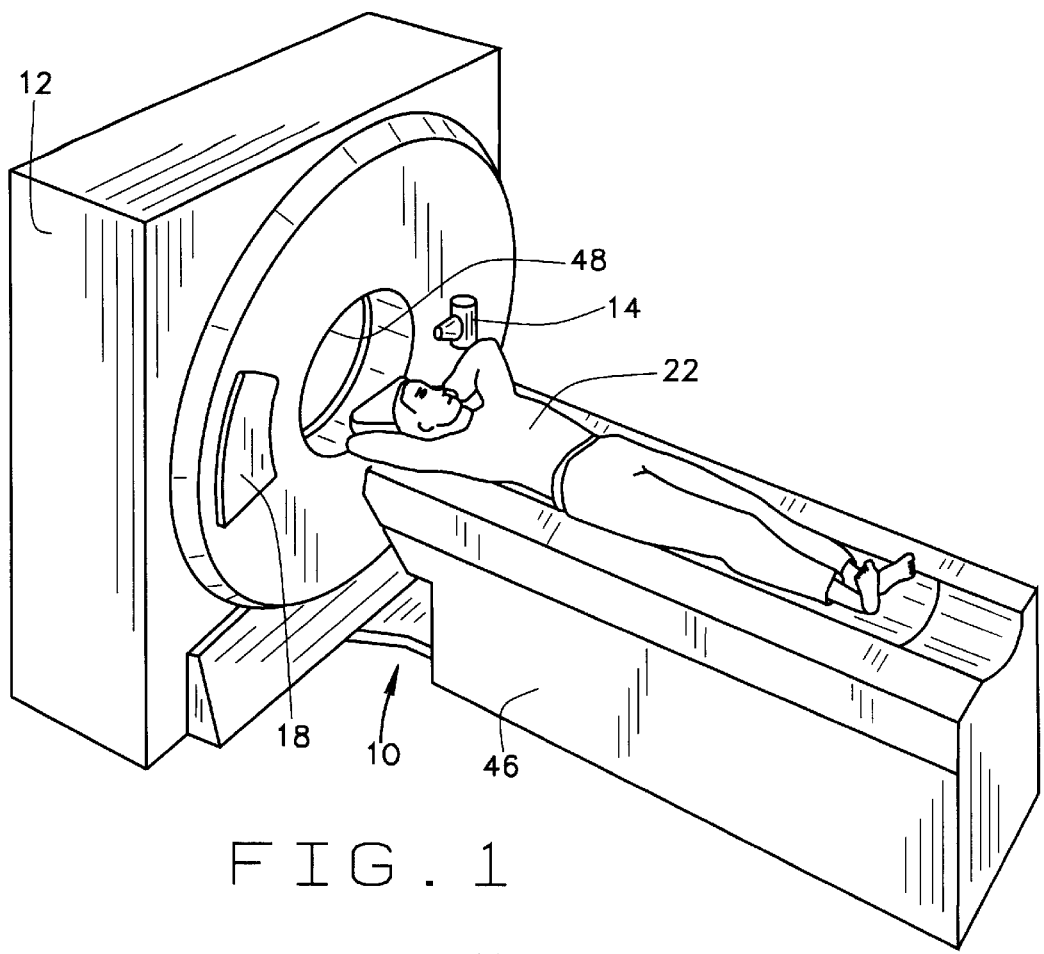
FIG. 1 is a pictorial view of a CT imaging system.
Figure 2:
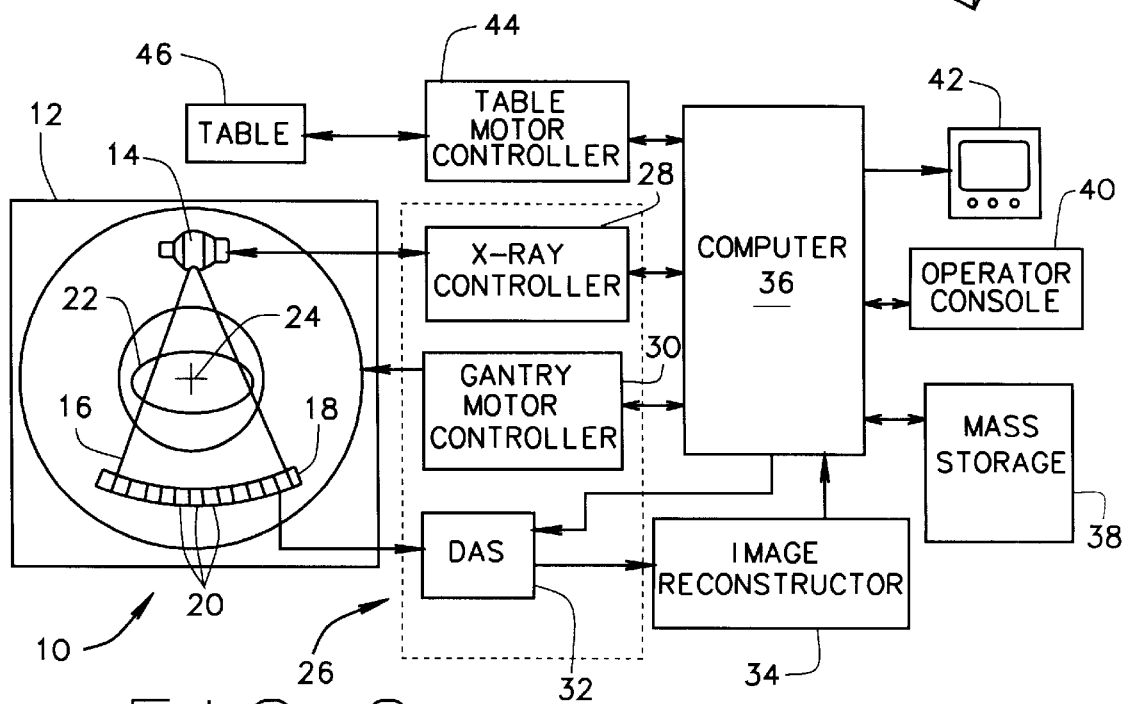
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
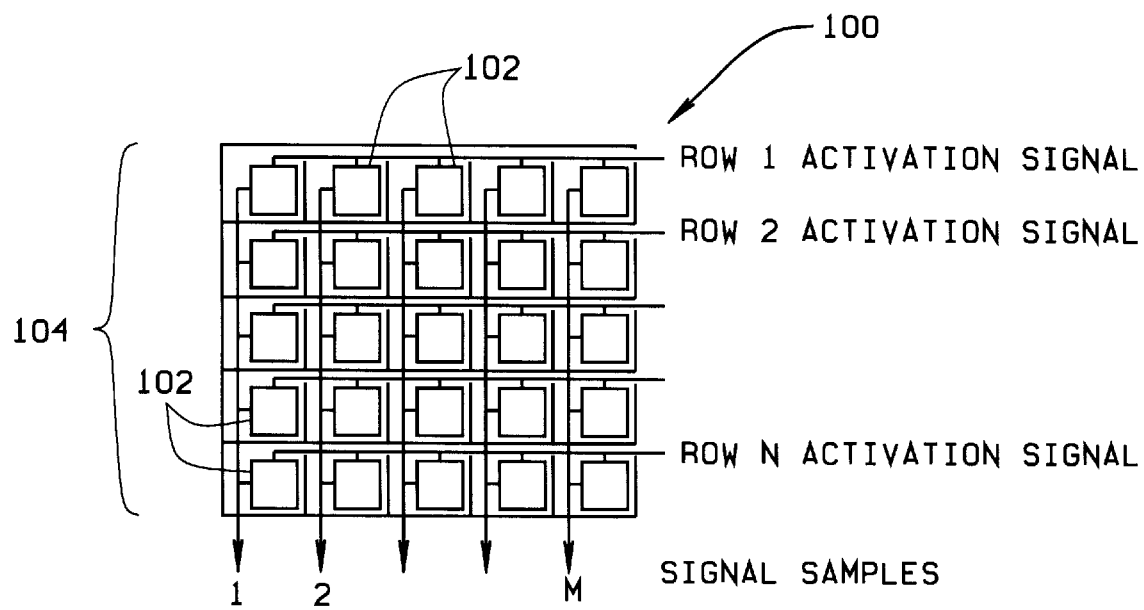
FIG. 3 is a top view of an exemplary a digital x-ray panel.

FIG. 3 is a top view of a digital x-ray panel 100. Panel 100 includes a plurality of detector cells 102 arranged in rows 104. Detector signals are sampled one row at a time by activating a trigger signal. The activation signals for row 1 to N are activated sequentially while all the cell signals for each row are read simultaneously.

Figure 4:
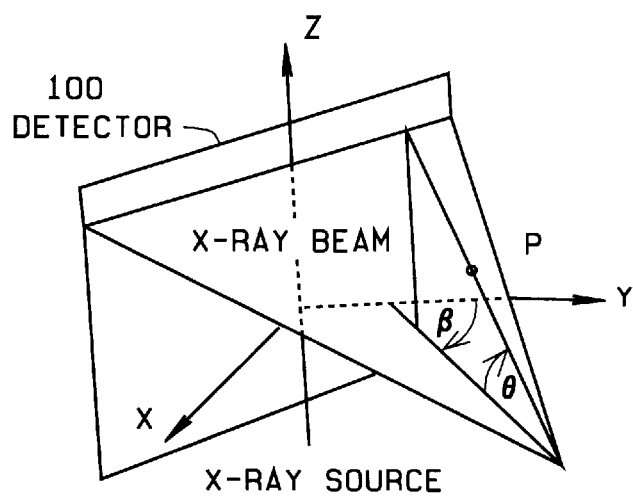
FIG. 4 illustrates sampling geometry for a cone beam.

Referring now to FIG. 4, the axis of rotation is the z-axis, and a rotating coordinate t is always parallel to the detector panel horizontal axis. With respect to detector 100, the panel activation lines (rows) are perpendicular to the z-axis (parallel to t-axis) and the panel read-out lines are parallel to the z-axis. In this configuration, the signals from each row are read out simultaneously.

Figure 5:
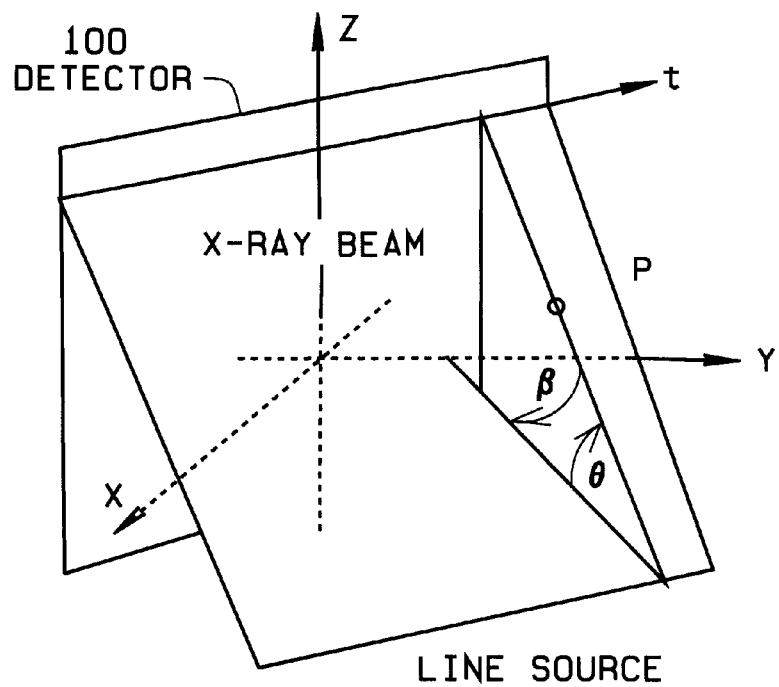
FIG. 5 illustrates sampling geometry for a tilted parallel beam.

In one embodiment of the present invention and referring to FIG. 5, rather than sampling all channels, or detector cells 102, in each detector row 104 simultaneously, detector panel 100 is rotated 90° so that all the signals of a constant t value (across z) are read out simultaneously. The sequence of the signal read-out across t is controlled in a similar fashion as in the fan-parallel sampling configuration.

Figure 6:
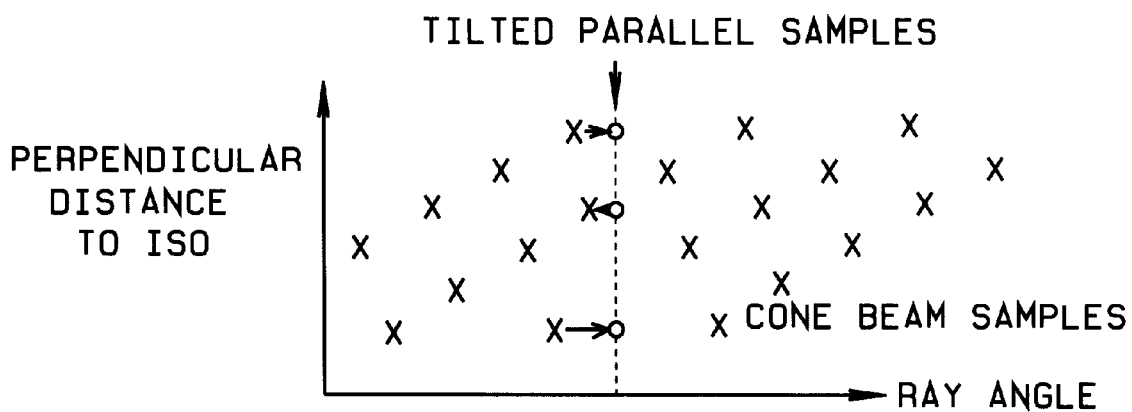
FIG. 6 illustrates a sampling pattern for cone beam to tilted parallel beam.

More specifically, a pre-defined delay triggering sequence is utilized to activate the signal activation line on panel 100. The delay sequence provides a set of parallel and tilted parallel samples. FIG. 6 illustrates a sampling pattern as viewed in a top-down fashion parallel to the z-axis. By properly delaying the sampling triggers, a set of tilted parallel geometry is obtained.

Once the projections are collected in a set of tilted parallel beam geometry, the scanned object density can be reconstructed by a new tilted parallel beam reconstruction algorithm. The derivation for the tilted parallel beam reconstruction formula can be carried out in a similar fashion as the derivation used in the Feldkamp cone beam reconstruction algorithm. The resulting equation for the reconstruction of an object, f(x,y,z), is:

$$f(x, y, z) = \frac{1}{2} \int_0^{2\pi} \left[ d / (d^2 + Z^2)^{1/2} \right] \left[ \int_{-\infty}^{\infty} S_\beta(\omega, Z) e^{j2\pi\omega x} |\omega| d\omega \right] d\beta$$

where:

$$S_\beta(\omega, Z) = \int_{-\infty}^{\infty} P_\beta(t, Z) e^{-j2\pi\omega x} dt.$$

$P_\beta$ (t,Z) is the projection intersecting point (x,y,z).

Unlike parallel beam reconstruction, the integration limits are from 0 to $2\pi$, primarily because the projections $\pi$ apart are no longer complementary rays for the tilted parallel case. However, similar weighting functions can be derived for the partially scanned samplings so that the data collection can be completed with $\pi$+fan angle.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Moreover, the system described herein performs an axial scan, however, the invention may be used with a helical scan although more than 360° of data are required. Accordingly, the spirit and scope of the invention are to be limited only by the terms of the appended claims.

What is claimed is:

1. A method for generating an image using a digital flat panel detector, the detector including a plurality of detector cells, a signal activation line provided for each cell row to activate each cell in each respective row, said method comprising the steps of:

obtaining data from the detector using a pre-defined delay triggering sequence;

using the obtained data to generate an image.

2. A method in accordance with claim 1 wherein the delay triggering sequence results in a set of parallel and tilted parallel samples.

3. A method in accordance with claim 1 wherein the image is generated using a tilted parallel beam reconstruction algorithm.

4. A method in accordance with claim 3 wherein an object, f(x,y,z), is:

$$f(x, y, z) = \frac{1}{2} \int_0^{2\pi} \left[ d / (d^2 + Z^2)^{1/2} \right] \left[ \int_{-\infty}^{\infty} S_\beta(\omega, Z) e^{j2\pi\omega x} |\omega| d\omega \right] d\beta$$

where:

$$S_\beta(\omega, Z) = \int_{-\infty}^{\infty} P_\beta(t, Z) e^{-j2\pi\omega x} dt, \text{ and}$$

$P_\beta(t,Z)$ is the projection intersecting point (x,y,z).

5. A processor for reconstructing an image using data collected from a digital flat panel detector, the detector including a plurality of detector cells, a signal activation line provided for each cell row to activate each cell in each respective row, said processor programmed to:

obtain data from the detector using a pre-defined delay triggering sequence;

generate an image using the obtained data.

6. A processor in accordance with claim 5 wherein said delay triggering sequence results in a set of parallel and tilted parallel samples.

7. A processor in accordance with claim 5 wherein said processor is programmed to generate an image using a tilted parallel beam reconstruction algorithm.

8. A processor in accordance with claim 7 wherein an object, f(x,y,z), is:

$$f(x, y, z) = \frac{1}{2}\int_0^{2\pi} \left[ d/(d^2+Z^2)^{1/2} \right]\left[ \int_{-\infty}^{\infty} S_\beta(\omega, Z)e^{j2\pi\omega x}|\omega| d\omega \right] d\beta$$

where:

$$S_\beta(\omega, Z) = \int_{-\infty}^{\infty} P_\beta(t, Z)e^{-j2\pi\omega x} dt, \text{ and}$$

$P_\beta(t,Z)$ is the projection intersecting point (x,y,z).

9. A computed tomography machine comprising:
a digital flat panel detector, said detector including a plurality of detector cells, a signal activation line provided for each said cell row to activate each said cell in each said respective row, and
a processor for reconstructing an image using data collected from said digital flat panel detector, said processor programmed to:
obtain data from the detector using a pre-defined delay triggering sequence;
generate an image using the obtained data.

10. A computed tomography machine in accordance with claim 9 wherein said delay triggering sequence results in a set of parallel and tilted parallel samples.

11. A computed tomography machine in accordance with claim 9 wherein said processor is programmed to generate an image using a tilted parallel beam reconstruction algorithm.

12. A computed tomography machine in accordance with claim 11 wherein an object, f(x,y,z), is:

$$f(x, y, z) = \frac{1}{2}\int_0^{2\pi} \left[ d/(d^2+Z^2)^{1/2} \right]\left[ \int_{-\infty}^{\infty} S_\beta(\omega, Z)e^{j2\pi\omega x}|\omega| d\omega \right] d\beta$$

where:

$$S_\beta(\omega, Z) = \int_{-\infty}^{\infty} P_\beta(t, Z)e^{-j2\pi\omega x} dt, \text{ and}$$

$P_\beta(t,Z)$ is the projection intersecting point (x,y,z).

* * * * *